(12) United States Patent
Quisenberry et al.

(10) Patent No.: US 8,414,631 B2
(45) Date of Patent: Apr. 9, 2013

(54) SYSTEM AND METHOD FOR COOLED AIRFLOW FOR DERMATOLOGICAL APPLICATIONS

(75) Inventors: Tony Quisenberry, Highland Village, TX (US); Niran Balachandran, Lewisville, TX (US); Sam K. McSpadden, Austin, TX (US); Christopher Alan Polser, Plano, TX (US)

(73) Assignee: ThermoTek, Inc., Flower Mound, TX (US)

( * ) Notice: Subject to any disclaimer, the term of this patent is extended or adjusted under 35 U.S.C. 154(b) by 0 days.

(21) Appl. No.: 12/524,592

(22) PCT Filed: Feb. 13, 2008

(86) PCT No.: PCT/US2008/053888
§ 371 (c)(1),
(2), (4) Date: Dec. 22, 2009

(87) PCT Pub. No.: WO2008/101034
PCT Pub. Date: Aug. 21, 2008

(65) Prior Publication Data
US 2010/0192596 A1 Aug. 5, 2010

Related U.S. Application Data

(60) Provisional application No. 60/889,723, filed on Feb. 13, 2007.

(51) Int. Cl.
*A61F 7/00* (2006.01)
*A61B 18/18* (2006.01)

(52) U.S. Cl. ............................ 607/107; 607/108; 606/20
(58) Field of Classification Search .......... 607/104–114; 606/20–25
See application file for complete search history.

(56) References Cited

U.S. PATENT DOCUMENTS

| | | | |
|---|---|---|---|
| 3,282,267 A | 11/1966 | Eidus | |
| 5,800,490 A * | 9/1998 | Patz et al. | 607/108 |
| 6,430,935 B1 * | 8/2002 | Klett et al. | 62/3.3 |
| 6,497,720 B1 * | 12/2002 | Augustine et al. | 607/96 |
| 6,581,400 B2 * | 6/2003 | Augustine et al. | 62/259.3 |
| 7,976,572 B2 * | 7/2011 | Ziaimehr | 607/96 |
| 2002/0026226 A1 * | 2/2002 | Ein | 607/108 |
| 2002/0058974 A1 | 5/2002 | Van Duren et al. | |
| 2002/0125001 A1 | 9/2002 | Kelly et al. | |
| 2004/0068310 A1 | 4/2004 | Edelman | |
| 2005/0000231 A1 * | 1/2005 | Lee | 62/3.5 |
| 2006/0034053 A1 | 2/2006 | Parish et al. | |
| 2006/0273646 A1 * | 12/2006 | Comiskey et al. | 297/408 |
| 2007/0106351 A1 * | 5/2007 | Ferguson et al. | 607/109 |

OTHER PUBLICATIONS

Young, Lee W., International Search Report for PCT/US 08/53888 as mailed Jul. 14, 2008 (2 pages).

* cited by examiner

*Primary Examiner* — Michael Peffley
*Assistant Examiner* — Adam Avigan
(74) *Attorney, Agent, or Firm* — Winstead PC

(57) ABSTRACT

A system and method of providing a temperature controlled gaseous medium for dermatological applications is described. The gaseous medium may be cooled and applied to an area such as a skin area to provide an analgesic effect thereon. The system and method also include an automated defrost cycle for minimizing the effects of decreased hydraulic diameter due to freezing.

8 Claims, 10 Drawing Sheets

SYSTEM AND METHOD FOR COOLED AIRFLOW FOR DERMATOLOGICAL APPLICATIONS

RELATED APPLICATIONS

The present application claims priority to and incorporates by reference the entirety of U.S. Provisional Patent Application No. 60/889,723, filed Feb. 13, 2007.

TECHNICAL FIELD

The present invention relates to gas cooling and, more particularly, but not by way of limitation to methods of and systems for providing cooled gas for dermatological applications.

RELATED ART

Conventional cooling technology typically includes passive cooling systems, compressor-based systems, and thermoelectric systems. In certain passive cooling systems, the air to be cooled is circulated over an air-to-air heat exchanger, which includes folded, finned heat exchangers, heat pipes, etc. The heat is then exchanged with the outside ambient air. As the amount of heat to be removed from the area increases, the size of the air-to-air heat exchanger increases. Compressor-based systems function by using a refrigerant and the cooling function is achieved by the compression and expansion of the refrigerant. Disadvantage of compressor-based systems include unwanted noise and vibration.

Thermoelectric temperature control systems use thermoelectric devices that pump heat using the Peltier effect. Typical thermoelectric devices incorporate a thermoelectric component utilizing electrical current to absorb heat from one side of the component and dissipate that heat on the opposite side. Thermal electric temperature control systems using thermal electric devices are, as described above, capable of both heating and cooling, low vibration, relatively high Coefficient Of Performance (ability to remove heat), low noise, and low profile.

It is known that dermal cooling may provide an analgesic effect such as a numbing of the surface of the skin to diminish pain caused by dermal procedures, such as, for example, laser or light-treatments and injections. To provide an analgesic effect by cooling a skin area, some approaches include the use of a cool object. Often the object is a piece of metal which has been placed first into a cooling medium, for example, a freezer or an ice bath before its use. Once the object has become sufficiently cold, the object may be removed from the cooling medium and placed on the skin surface to provide an analgesic effect. Such approaches have disadvantages. If these objects are cooled to temperatures below freezing to allow them to maintain temperatures below ambient for longer periods of time, problems may result from improper use. For example, one problem that may arise when temperatures below freezing are applied to a skin area is that cellular damage may occur.

Medical care providers thus recognize the need to provide carefully selected warmth and/or cooling directly to patients as part of their treatment and therapy. For example, anesthetic properties have been reported using cold therapy for dermatology patients. Several devices have been developed that deliver temperature controlled fluids and gasses to achieve various benefits. Typically, these devices have a heating or a cooling element, a pump for causing the air or fluid to flow, and a thermal interface between the patient and the temperature controlled fluid. One traditional way has been heating or cooling blankets directing a conditioned gas toward a covered person through a multiplicity of orifices in one side of the blanket.

Other methods for cooling the temperature of a surface have been developed such as a roller with a cooling substance contained therein. Other pain management devices have used cooling devices that have a handle and a cooling head, where the handle contains a cooling substance to cool the head as it contacts a surface.

Both pre-procedure and post-procedure dermal cooling has been utilized to protect the skin from damage from light sources used during such procedures as laser hair removal and skin peeling. Contact coolers that cool the skin through direct contact therewith have the disadvantage of not allowing the laser to operate on the skin while the contact cooler was contacting the skin. In the past, air coolers were not precisely controlled and would provide air an output of a delivery hose that was below freezing temperatures, for example, −10 to −13° C. The users of such systems had to spatially dispose the output from the skin surface in order to avoid the deleterious effects of freezing the skin. This added another level of inaccuracy to the system.

BRIEF SUMMARY OF THE INVENTION

One aspect of an illustrative embodiment of the present invention relates to gas coolers for dermatological applications. More particularly, one aspect of an illustrative embodiment relates to a method of and system for cooling a gaseous medium to a specified temperature and making it available for cooling surfaces, such as, for example, skin surfaces. In various embodiments, the cooled gas or other gaseous or fluidic medium is pumped from a control unit via an insulated hose. The control unit may increase or decrease the temperature of the cooled gas depending on user inputted settings. In some embodiments, the control unit may monitor the temperature of the gas exiting the control unit and calculate the temperature of the gas exiting the insulated tube based on various criteria including, among other things, the pressure and velocity of the gas leaving the control unit and the pressure and temperature of the environment surrounding the delivery hose.

In various embodiment a method for thermally affecting a gaseous medium for dermatological applications is shown, the method including providing a plurality of thermally controlled flow tunnels; creating a pressure differential to impart airflow through a plurality of flow tunnels for thermal interaction therewith; actively cooling the plurality of flow tunnels to a temperature below a freezing point of moisture contained within the gaseous medium; monitoring a condition relating to the airflow of the gaseous medium flowing through the flow tunnels; and reducing the level of active cooling of at least one of the plurality of flow tunnels in response to a monitored condition indicative of a reduction in a hydraulic diameter of at least one of the plurality of flow tunnels.

In various embodiments, a system for providing a cooled gaseous medium for dermatological applications is shown, the system including a plurality of flow tunnels having inlets and outlets; an air mover adapted to impart airflow to a gaseous medium through the plurality of flow tunnels; a plurality of thermoelectric coolers thermally coupled to the plurality of flow tunnels and adapted to actively remove heat therefrom to cool the gaseous medium flowing therethrough; a sensor adapted to monitor at least one indicator relative to the flow of the gaseous medium through the plurality of flow tunnels and send a signal if a hydraulic diameter of at least one of the plurality of flow tunnels decreases; and wherein the amount of heat being actively removed by at least one of the plurality of thermoelectric coolers from at least one of the plurality of flow tunnels is reduced in response to the signal.

In some embodiments, the control unit cools a gas such as, for example, ambient air by passing it through heat transfer assemblies. The heat transfer assemblies may have flow tunnels comprising a plurality of microtubes running therethrough, the microtubes having a plurality of microchannels formed along inside surfaces thereof for enhancing the transferring of heat from air passing therealong. The flow tunnels may be in thermal communication with thermoelectric coolers (TEC). In some embodiments, the heat transfer assemblies are monitored to detect if an area inside the microtubes is being blocked by a buildup, such as freezing moisture, causing a decrease in the hydraulic diameter of the microtubes. In response, various embodiments will lower the amount of cooling being applied to the flow tunnels until the frozen moisture has been cleared.

Various embodiments are adapted to provide precise dermal cooling using a relatively small, relatively light unit that produces relatively little noise and relatively low vibrations. Another aspect of various embodiments is to provide precisely controlled dermal cooling by providing a cooled gas maintained at temperatures just above freezing to prevent cellular damage caused when cells are exposed to below freezing temperatures.

BRIEF DESCRIPTION OF THE DRAWINGS

A more complete understanding of the methods and systems of the present invention may be obtained by reference to the following Detailed Description when taken in conjunction with the accompanying Drawings wherein.

DETAILED DESCRIPTION OF THE DRAWINGS

When a temperature of a patient's skin is lowered, a topical anesthetic effect may be experienced resulting in less pain experienced by the patient during many typical dermatological procedures. The anesthetic effects may become noticeable on skin that has been cooled to a temperature of about 20° C. or less. In addition to the anesthetic aspects, cooling a skin surface may also minimize peripheral skin damage during dermatological procedures, such as, for example, laser skin treatments.

A typical non-cooled skin temperature is about 32° C. If the skin temperature can be reduced quickly to about 20° C., the topical anesthetic effect noted above can be induced quickly and the dermatological procedure performed more rapidly, thereby permitting more patients to be treated in a given period of time. Use of gas to cool a skin surface may avoid problems such as distortion of laser light being applied to the patient's skin and excess water being applied to the patient and adjacent areas. During dermal application involving the use of lasers, the laser may be utilized to heat collagen underneath the skin in order to stimulate the formation of new collagen or to burn the pigment of dead follicles. When a dermal coolant lowers the temperature of the skin too much, the efficacy of the laser may be diminished by cooling too deep into the dermis.

Figure 1:
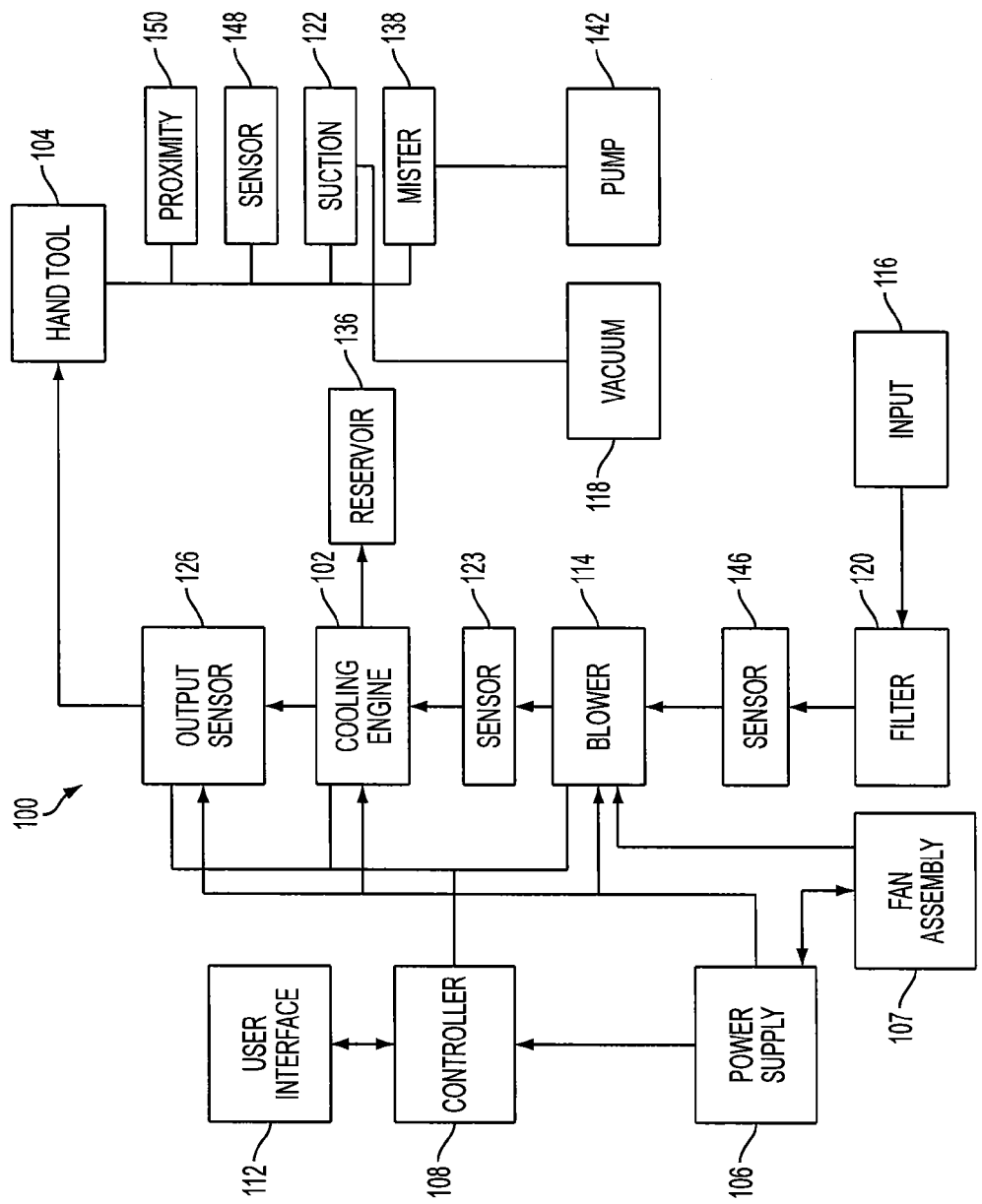
FIG. 1 is a schematic of an air cooling system in accordance with an embodiment of the present invention.

FIG. 1 shows a system 100 which may be used to provide cooling for dermatological applications, such as, for example, laser treatments, contour surfacing, hair removal, and other applications where cooling may be desirable. The system 100 may also be used in other medical applications, such as, for example, treating patients suffering from hypothermia. The system 100 has a cooling engine 102 for removing heat from a gaseous medium flowing therethrough. The gaseous medium being cooled may include a gas, such as an inert gas, a mixture of gases, such as air or ambient air, a gas containing moisture, such as humidity, a vapor, or any other medium having gas-like properties. The terms "air," "airflow," or any combination of words related to the term air, as used herein, should be broadly interpreted as referring to any gaseous medium having gas-like properties, and is not used and/or presented herein as limited to ambient air or atmospheric air.

In various embodiments, the cooling engine 102 includes one, some, or none of the following: one or more Peltier elements, one or more heat sinks, and one or more cooling fans. The cooling engine 102 receives a gaseous medium from an air mover 114. The term air mover as used herein is being used in a generic sense to refer to any device capable of creating a pressure differential, such as, for example, but not by way of limitation, a blower, a fan, a vacuum, a turbine, or any other device capable of causing a volume of gas to move. In the embodiment shown, the air mover 114 is disposed before the cooling engine 102 and directs the gaseous medium therethrough by creating a positive pressure at an entrance or inlet of the cooling engine 102. However, in some embodiments, the air mover 114 is disposed after the cooling engine 102 and directs the gaseous medium therethrough by creating a negative pressure at an exit or outlet of the cooling engine 102.

After being cooled by the cooling engine 102, the cooled gas then flows to a hand tool 104 having an output for supplying the cooled gas to a skin surface. The cooling engine 102 may be connected to a controller 108. In some embodiments, a user interface 112, including a display and/or an input, is connected to the controller 108. The air mover 114 receives the gaseous medium from an input chamber 116 which, in some embodiments, has a filter 120 for filtering the gas as it enters and/or leaves the input chamber 116. In some embodiments, the filter 120 may include a noise filter or silencer for dampening noise. The cooling engine 102 may also be in fluid communication with a reservoir 136 for collection of water resulting from the cooling of the air passing therethrough. The cooling engine 102 and the controller 108 and the air mover 114, among other components, may be powered by one or more power supplies 106. In some embodiments, one power supply 106 supplies power to all the components of the system 100. In various embodiments, a plurality of power supplies 106 supply power to various components of the system.

Referring now to the hand tool 104 in more detail, cooled gas from the cooling engine 102 is outputted at the gas output of the hand tool 104 and applied to the patient's skin. In some embodiments, a vacuum 118 may be utilized to reduce the amount of debris resulting from a dermatological procedure. In some embodiments, the hand tool 104 may include a skin temperature sensor 148 and/or a skin proximity sensor 150. The skin temperature sensor 148 may measure the temperature of the skin area being cooled and send the information to the controller 108. In some embodiments, the information is used to adjust the temperature of the cooled gas being provided, for example, in a feedback loop. In some embodiments, the information is displayed on a user-readable display. The system 100 may also include a vacuum 118 interoperably connected to the hand tool 104 for removing the gaseous medium provided, ambient air disposed near the cooled area, and any debris on or near the area. In some embodiments, the input chamber 116 and the filter 120 may be used in conjunction with the vacuum 118. Additionally, a waste canister 134 may also be used to collect the debris from the hand tool 104, for example, from a patient's skin during a micro-dermabrasion or laser peel procedure. In some embodiments, a reduced amount of energy is consumed when the cooled gaseous medium is reclaimed after delivery to the patient.

The hand tool 104 may also be adapted to include a coolant output or mister 138 to apply water or other coolant substance (e.g., a liquid or gel) to the skin of the patient. The coolant output 138 may be interoperably connected to a valve to control the amount of coolant applied via the coolant output to the skin of the patient. The coolant may be supplied by a pump 142, for example a water pump. The amount of coolant applied to a patient may be controlled by the controller 108 or may operate independent of the controller 108, for example by a valve having user input controls. In some embodiments, the pump 142 may not be needed if the force supplied by the air mover 114 is great enough to transport water to a skin surface in addition to the cooled gaseous medium supplied. In various embodiments, the pump 142 may utilize the liquid from the reservoir 136 as the coolant substance supplied to the mister 138. In some embodiments, a UV light or other viricide or bactericide treatment is used to sanitize the liquid in the reservoir 136.

Still referring to various embodiments related to the hand tool 104, a coolant output may be used to provide additional topical anesthetic effect via, for example, evaporative cooling. In some embodiments, a skin temperature sensor is utilized to provide feedback to the user and to the controller 108. In some embodiments, a proximity sensor may provide feedback to the user so that the hand tool 104 is positioned by the user at an optimal distance from the skin of the patient. In some embodiments, the hand tool 104 may also include a laser used for laser dermatological applications or other tools used in dermatological applications. In other embodiments, the hand tool 104 may include attachment points adapted to connect a laser thereto. The source of the laser may be located at the hand tool 104, or may be remotely disposed from the hand tool 104 and optically connected therewith.

Referring now to the system 100 in general. The system 100 is adapted to precisely control the temperature and pressure of the gaseous medium being supplied to the hand tool 104. In various embodiments, a output sensor 126 is disposed between the cooling engine 102 and the hand tool 104 to monitor the temperature and pressure of the gaseous medium after cooling. The output sensor 126 may be located near the cooling engine 102 and adapted to provide temperature and pressure information for use in determining the temperature of the gaseous medium at a remote location, such as at the exit of the hand tool 104. In some embodiments, an algorithm is used based on the characteristics of a delivery hose used to deliver the gaseous medium to the hand tool 104, such as, for example, length of the delivery hose and insulating capabilities of the hose, such as, the thermal conductivity of the material used to make the hose. As will be explained further below, the delta-T ($T_2$-$T_1$) between the exit of the cooling engine 102 and the exit of the hand tool 104 can be determined based on one or more of the following observable conditions: the temperature of the gas flowing in the hose, the pressure of the gas flowing in the hose, the ambient temperature outside of the hose, the insulating properties of the hose, and the length of the hose. For example, the input chamber 116 may include a temperature sensor to measure the temperature of the ambient air for use in the above-mentioned calculations.

In the system 100, the controller 108 may be used to vary the flow rate of the gaseous medium flowing through the cooling engine 102. The controller 108 may also precisely control the temperature to which the cooling engine 102 cools the gaseous medium flowing therethrough. In various embodiments, the system 100 is adapted to run on a variety of inputted AC or DC voltage ranges, for example, off a DC power source ranging from, on the order of 150-340 $V_{dc}$ or AC power source ranging from, on the order of 95-250 $V_{ac}$. In some embodiments, the temperature to which the gaseous medium is cooled is varied by varying the amount of power supplied to the Peltier devices (or TEC arrays) by the power supply 106. The power supply 106 driving the TEC array's may have variable output of between, for example, on the order of 5-135 $V_{dc}$ which can be varied by the controller using, for example, a Pulse Width Modulation (PWM) signal. By varying the output of the power supply 106, the power to the TEC arrays can be modulated to achieve precise temperature control. Varying the output also allows the HTA module to use a minimum amount of input power while providing optimal control, lowering the overall input power required by lowering the drive voltage.

In some embodiments, the cooling engine 102 may be a solid-state heat pump, referred to above as a Peltier device or a TEC device. When the cooling engine 102 is operated in a cooling mode, the direction of electrical current applied to one or more Peltier elements of the cooling engine 102 is chosen so as to cause a side of the one or more Peltier devices in thermal contact with one or more flow tunnels to remove heat therefrom. The one or more flow tunnels may have a gaseous medium flowing therethrough and in thermal contact therewith. When the one or more Peltier devices remove heat from the one or more flow tunnels, heat is thereby removed from the gaseous medium flowing therethrough and the gaseous medium is cooled thereby. When in operation, heat removed by the one or more Peltier elements must be rejected to the ambient environment. As will be explained in greater detail below, in various embodiments, one or more heat sinks thermally coupled to the one or more Peltier devices and operating in conjunction with one or more cooling fans facilitate rejection of the removed heat to the ambient environment. As will be explained in more detail below, the system may also include a defrost cycle. In various embodiments, the system 100 monitors various conditions to detect whether a hydraulic diameter of the flow tunnels has been reduced by, for example, frozen moisture from the gaseous medium passing therethrough. In some embodiments, the gaseous medium to be cooled is drawn from the ambient are around the system 100. When the TEC arrays actively cool, or actively remove heat from, the flow tunnels, moisture, usually in the form of water, may be deposited on an inside portion of the flow channels. When the TEC arrays actively cool the flow tunnels to a temperature below a freezing point of the moisture contained therewithin, the moisture may freeze, or solidify, and deposit onto the inside of the flow tunnels thereby reducing a hydraulic diameter thereof. The water, When it is determined that the hydraulic diameter has decreased by a predetermined amount, the system may decrease the amount of power supplied to at least one of the one or more Peltier devices until the frozen moisture has been reduced and the hydraulic diameter returned to at or near a normal operating size. In some embodiments, the electric current supplied to at least one of the one or more Peltier devices may be reversed thereby actively heating the at least one of the one or more Peltier devices.

For the defrost cycle, the air velocity coming out of the device is monitored by measuring the pressure. In various embodiments, when the control unit is turned on, the control unit will do an auto-calibration of the pressure. The expected pressure at that particular altitude will be compared to factory set parameters. At each power-up thereafter, the control unit will run a calibration check to make sure everything is operating correctly.

As noted above, the cooling engine 102 includes an output sensor 126. The controller 108 may use information, such as temperature and pressure, monitored by the output sensor 126 along with other information in an algorithm to make determinations, such as, for example, how much power should be supplied by the power supply 106 to drive the cooling engine 102 to reach a particular temperature in a particular amount of time. In some embodiments, feed back from the output sensor 126 is used to adaptively adjust the amount of power applied to the cooling engine 102 to reach a desired temperature in a desired amount of time and also to maintain the desired temperature.

In some embodiments, the system 100 may also be used to treat hypothermia by heating the patient's skin, for example, to 33-35° C. In order to heat a gaseous medium passing through the cooling engine 102, current applied to the one or more Peltier elements of the cooling engine 102 is reversed relative to that applied when the cooling engine 102 is used to cool the gaseous medium. In some embodiments, an air blanket or the like (not shown) may be used in place of the hand tool 104 to apply the warmed gaseous medium to the patient. The air blanket may be used to circulate the warm gas around one or more portions of the patient's body. When used as a heating device, recirculation of heated gas from the air blanket back to the cooling engine 102 may be employed as dictated by various design considerations.

Referring again to the system 100 in general, various embodiments are adapted to provide a cooled gaseous medium at a temperature just above freezing in order to only cool a top layer of a skin surface, such as the thin microns of the subdermis to numb the nerve fibers proximately disposed there. Various embodiments are adapted to provide the cooled gaseous medium without the use of a compressor. In various embodiments, the system 100 is adapted to provide the cooled gaseous medium to a remote location, for example a remotely disposed skin surface, at between on the order of 0 and 3° C. In some embodiments, a solid-state cooler is provided capable of accurately providing a cooled gaseous medium at a flow velocity of over 1000 liters per minute. In various embodiments, a standby mode is utilized where the temperature of the gaseous medium is provided at a constant temperature, for example, around, on the order of, 10° C. From the standby mode, upon activation, various embodiments may be capable of providing a cooled gaseous medium to a remote location at between, on the order of, 0 and 3° C. within 90 seconds and in some embodiments, as little as 60 seconds. Various embodiments are adapted to provide continuous therapy for a full day of treatment without needing to be defrosted. In some embodiments, an automatic internal defroster is provided that automatically defrosts to keep the device from freezing up.

Figure 2:
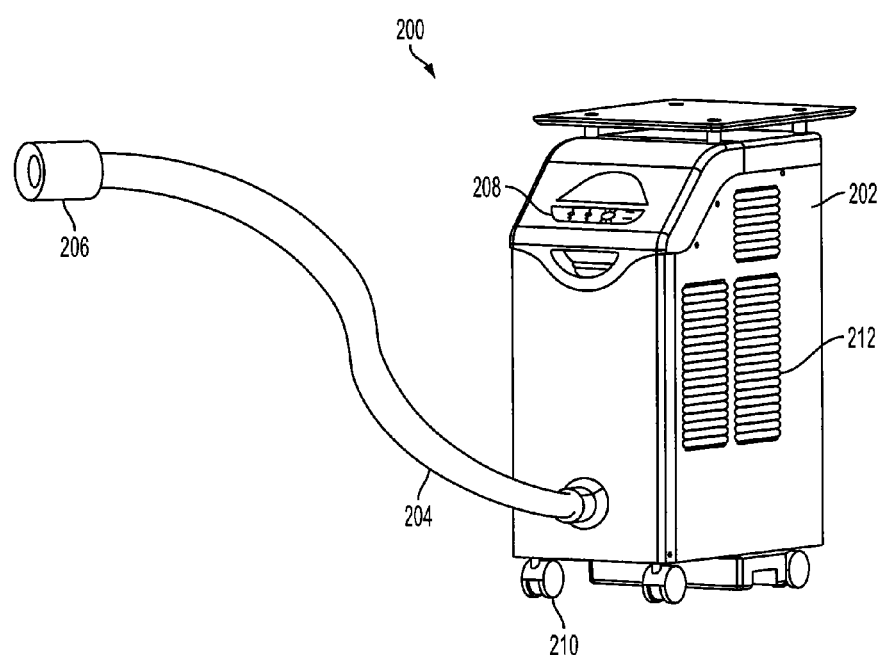
FIG. 2 is a diagram of an illustrative embodiment of the system of FIG. 1.

Referring now to FIG. 2, a system 200 is shown according to an embodiment. The system 200 has a control unit 202 with a delivery hose 204 connected thereto. The control unit 202 cools a gaseous medium that then flows through the delivery hose 204 to an exit 206. The exit 206 may be connected to a hand unit (not shown) for assisting a user in controlling and directing the airflow out of the exit 206. In some embodiments, a shut-off valve may be located along the delivery hose 204, wherein the shut-off valve is adapted to allow a user to discontinue the airflow out of the exit 206 without having to return to the control unit 202. In some embodiments, the shut-off valve may be monitored and, for example, the gaseous medium could be internally circulated, for example, by opening a valve so the gaseous medium may flow from the bottom chamber to the top chamber.

Various embodiments may use a plurality of different hose sizes and types to transport the cooled gaseous medium to the skin surface. Various hoses may be more rigid, while other hoses may be more light weight or more flexible. In various embodiments, a hand piece (not shown) may be attached to the end of the delivery hose 204 to facilitate administration of the cooled air. The hand piece may be adapted to accommodate a plurality of different nozzles that can be attached to the delivery hose 204 or to the hand piece, such as a nozzle for delicate cooling, for example, around a facial region, or a nozzle for large-area cooling, such as on a back region. In various embodiments, the flow rate can be variably controlled by one, both, or neither of the controller or the nozzle, for example, so that the airflow can be turned down while cooling a facial region and turned up while cooling a back region. Various embodiments may have indicators for alerting the user that the airflow through the delivery hose 204 may be blocked, for example, by a kink in the delivery hose 204.

The control unit 202 also has a user interface 208 where a user may change various settings such as the temperature and/or the flow rate of the gaseous medium being provided. In the embodiment shown, the control unit 202 has wheels 210 disposed on a lower portion thereof for facilitating movement of the control unit 202. It can also be seen that the control unit may have vent slats 212 disposed on one or more surfaces thereof. In the embodiment shown, the vent slats 212 are located on a side panel of the control unit 202. As will be explained in more detail below, the vent slats 212 may allow ambient air to pass therethrough.

Figure 3:
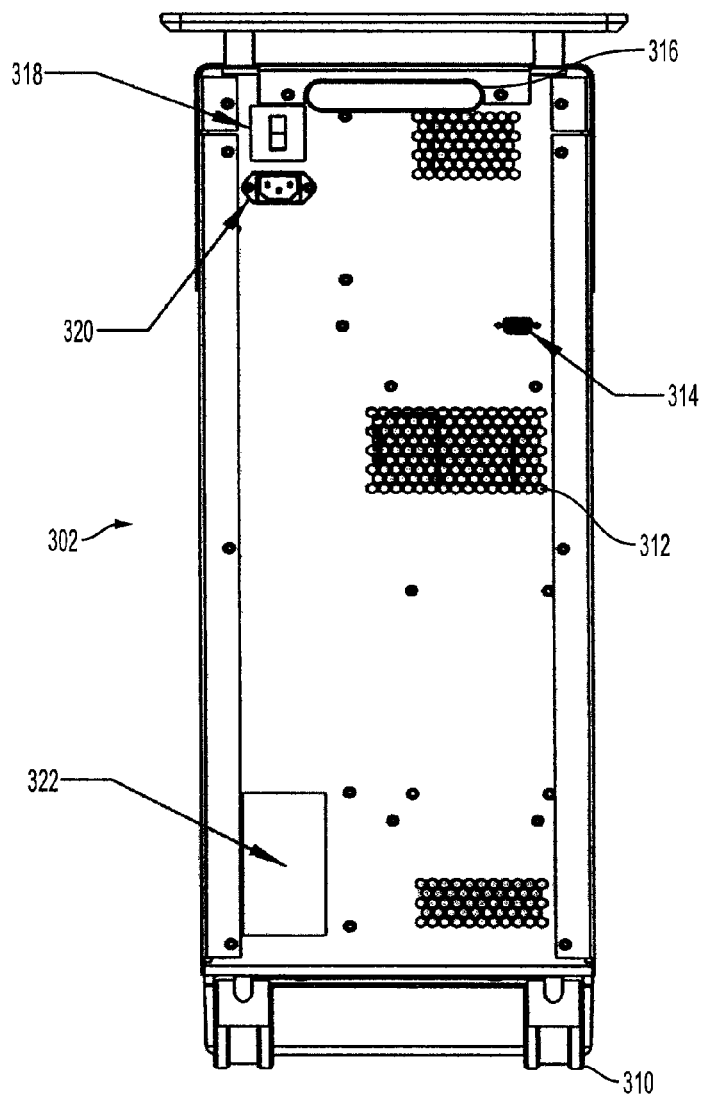
FIG. 3 is a rear view of FIG. 2.

Referring now to FIG. 3, a rear view of a control unit 302 is shown. Wheels 310 can be seen disposed on a lower portion of the control unit 302. Air vents 312 can also be seen disposed on various portions of a rear panel of the control unit 302. A communication port 314 can also be seen. In some embodiments, the communication port 314 may allow the control unit 302 to send and/or receive signals from other electronic devices. The communication port 314 may be a USB port, a serial port, an Ethernet port, an RS485 ports, an RS232, an antenna for sending and receiving wireless signals, or any other input/output port for sending and/or receiving signals. A transport handle 316 disposed on the rear panel of the control unit 302 can be seen. In the embodiment shown, the transport handle 316 is disposed on an upper portion of the rear panel, but the transport handle 316 may be located anywhere on the control unit 302. A power switch 318 for turning the control unit 302 on and off can be seen. The power switch 318 may be located anywhere on the control unit, but in the embodiment shown, it is disposed on an upper portion of the rear panel. The power switch 318 may include a circuit breaker such as, for example, a ground fault circuit interrupter. A power-entry module 320 is also shown disposed on a rear panel of the control unit 302. An intake opening 322 can also be seen. The intake opening 322 may also have a filter 324, such as, for example, a HEPA filter. In some embodiments, the intake opening 322 is where all, some, or none of the gaseous medium to be cooled by the control unit 302 enters. The filter 324 may be utilized to ensure the gaseous medium to be cooled is relatively clean and relatively free of particulate or other debris. A sill be explained further below, the intake opening 322 may be in flow communication with a noise filter. In the embodiment shown, the intake opening 322 is located near a lower portion of a rear portion of the control unit 302, however the intake opening 322 may be located anywhere on the control unit 302. In some embodiments, the intake opening 322 also includes one or more connectors to connect to a supply hose that supplies a gas or other medium.

Figure 4:
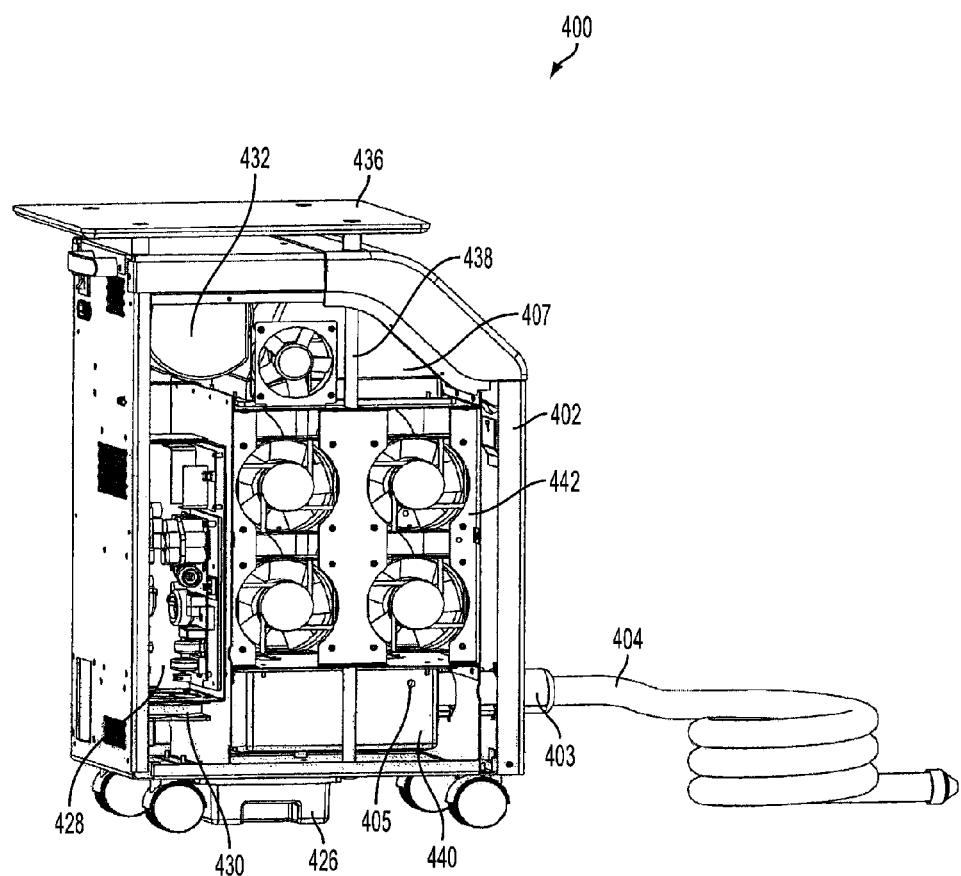
FIG. 4 is a side view of FIG. 2, having a side panel removed.

Referring now to FIG. 4, an cooling system 400 is shown where a control unit 402 is shown with a side panel removed for descriptive purposes. A delivery hose 404 is attached to a hose interface 403. The hose interface 403 may be a quick connect type interface, may have screw races, or may include any other way of connecting the delivery hose 404 to the control unit 402. A drip pan 426 can be seen attached to an underneath portion of the air cooler system 400. The drip pan 426 may be used to catch condensate resulting from the cooling done by the cooling engine. One characteristic of gases and moisture therewithin is that a gas at a higher temperature may hold a larger quantity of moisture therewithin. As the gas is cooled from a first higher temperature to a second lower temperature, moisture suspended therewithin will no longer remain suspended therewithin and will begin condensating. An increasing amount of moisture will condensate as the temperature of the gas is lowered. The drip pan 426, disposed on a lower portion of the control unit 402, is adapted to capture the moisture as condensation occurs as a result of the cooling of the gaseous medium. In some embodiments, the drip pan 426 is a removable tray for ease of emptying. In some embodiments, the drip pan 426 includes a drain hose for draining the condensate therefrom.

As previously mentioned, the control unit 402 may utilize thermoelectric cooler (TEC) arrays to cool a gaseous medium. A power source 428 disposed within the control unit 402 is adapted to power, among other things, the controller, the TEC arrays, and various fans and/or pumps. In some embodiments, a plurality of power sources may be utilized to power various electrical components. In some embodiments, one or more power supplies are used to power the TEC arrays and do not power any other components. In some embodiments, a fan assembly 430 may be included to cool the power source 428. An air mover 432, such as a blower, is disposed within control unit 402 for blowing a gaseous medium past the heat transfer assembly (HTA) modules 442 and through the delivery hose 404. A fan 434 may also be included to cool the air mover 432. In some embodiments, the temperature of the air mover 432 is monitored and the fan 434 is used to modulate the temperature of the air mover 432. A table top 436 may be disposed above an upper portion of the control unit 402. A support 438 may be utilized to support the weight of one or more objects placed on the table top 436. Below the HTA module 442, a bottom chamber 440 can be seen. Sensors 405 and 407 can be seen disposed above and below the HTA module 442. In some embodiments, the sensors 405 and 407 may monitor temperatures and pressures of the gaseous medium being cooled by the HTA module 442.

Figure 5:
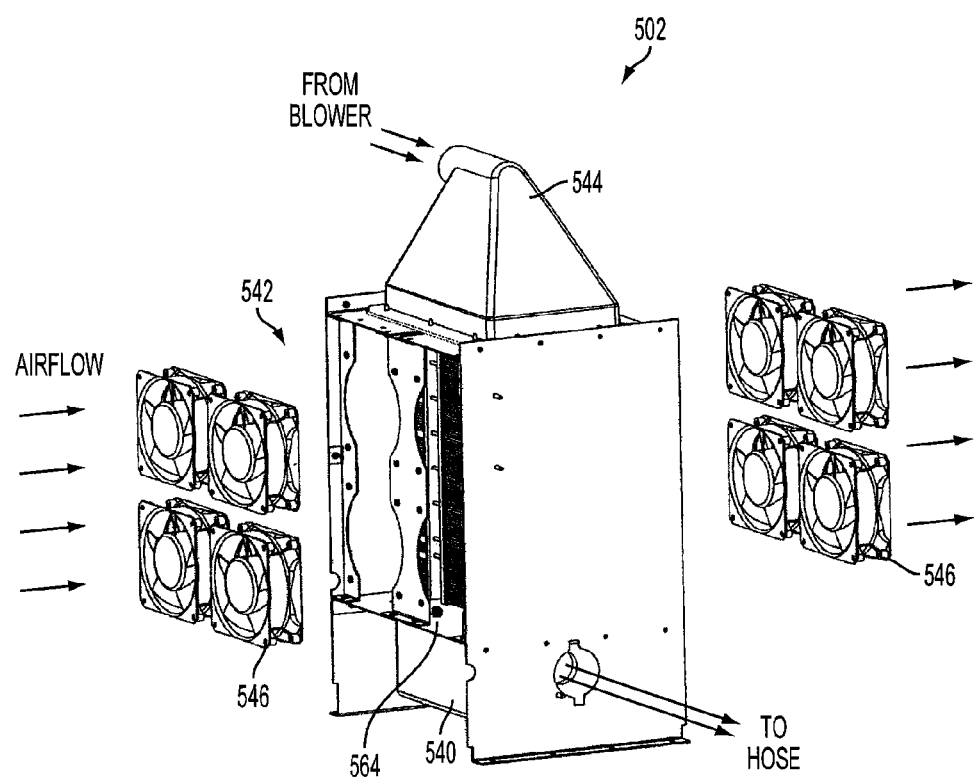
FIG. 5 is an exploded view of a cooling device.

Referring now to FIG. 5, an exploded view of a portion of a control unit 502 is shown. The gaseous medium from an air mover, such as a blower (not shown), enters a top chamber 544. The gaseous medium passes through a plurality of HTA modules 542 to be cooled and down to a bottom chamber 540. The cooled gaseous medium then proceeds to the delivery hose 504 for use in a dermatological applications. A plurality of fans 546, exploded for descriptive purposes, may be disposed on one, both, or neither side of the HTA modules 542 to provide a flow of ambient air thereacross to remove heat therefrom. In some embodiments, the plurality of fans 546 may be disposed in a push-pull relationship relative to the HTA modules 542 in order to provide an increased flow of ambient air thereacross to remove heat therefrom.

Figure 6:
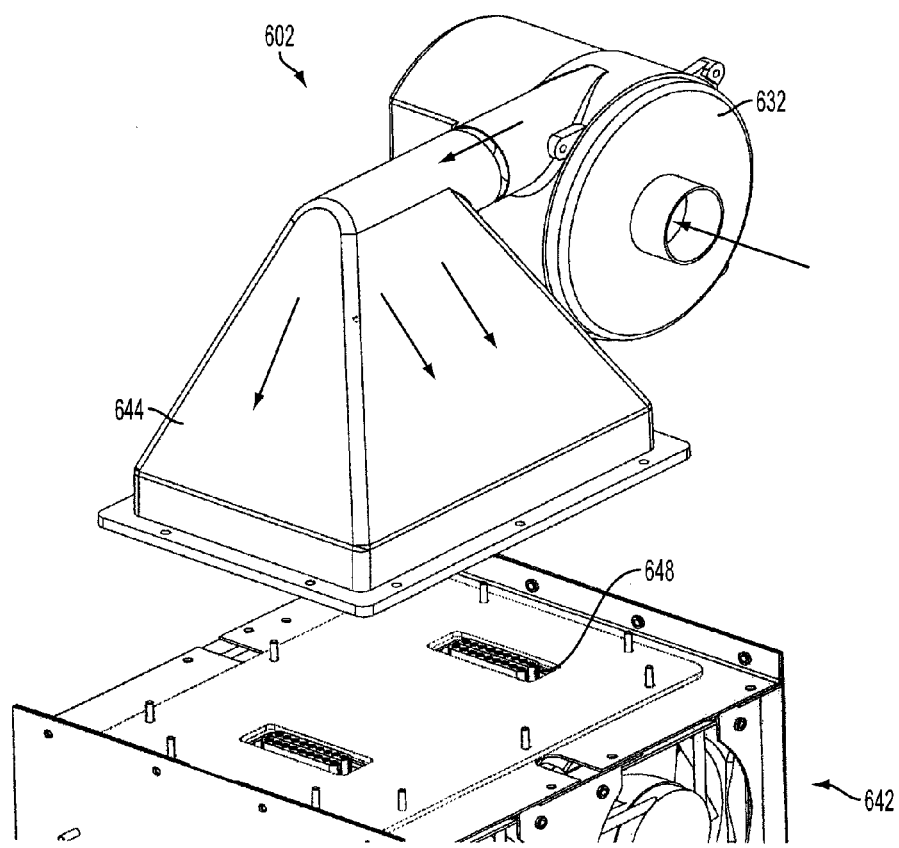
FIG. 6 is an exploded view of a chamber.

Referring now to FIG. 6, an exploded view of a top portion of a control unit 602 is shown. The gaseous medium enters the air mover, such as a blower, 632 and is blown into the top chamber 644. As previously mentioned, in some embodiments, the air mover 632 may create either a positive pressure of a negative pressure relative to the HTA modules 642. As can be seen from the embodiment shown, the top chamber 644 expands from a narrow entrance opening to a large exit opening. Having a large exit opening creates an area of low pressure relative to the entrance opening. This low pressure area above the HTA modules 642 helps create an environment conducive to turbulent flow. By expanding the area of the top chamber 644, a back-pressure against the air mover 632 can be minimized The gaseous medium then flows into the flow tunnels 648 of the HTA modules 642.

There is an upper chamber 644, such as an intake manifold, over a plurality of flow tunnels 648. The top chamber 644 is monitored to look at the airflow based on the characteristics of the air mover 632. The control unit 602 may utilize an air mover 632, such as one or more of a blower, a pump, a vacuum, a positive displacement pump, a centrifugal pump, a turbine-style magnetically coupled pump, or any other device for creating a pressure differential.

Figure 7:
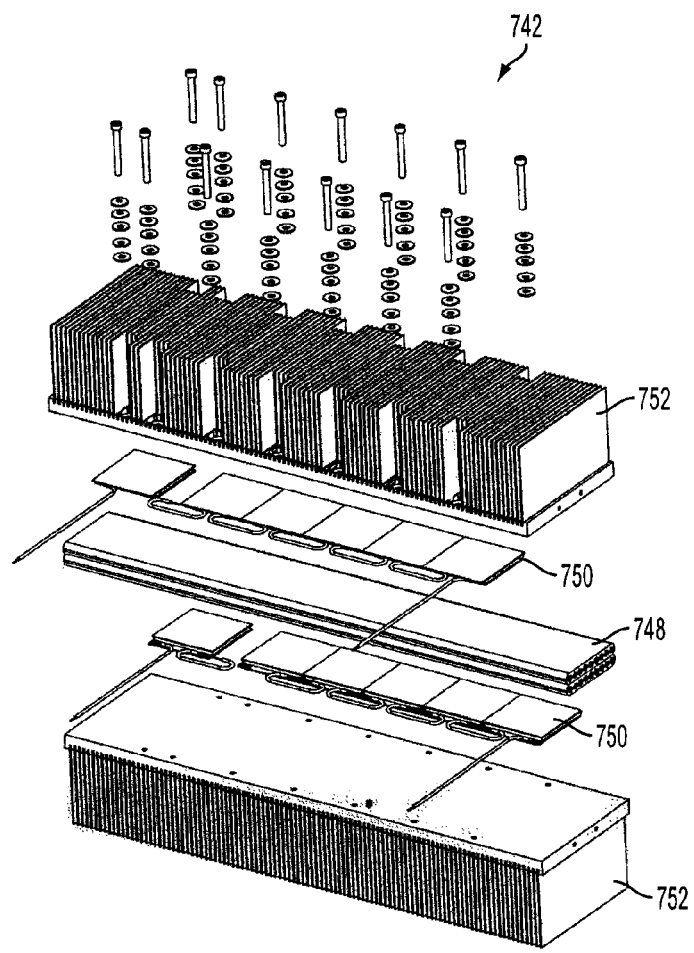
FIG. 7 is an exploded view of a heat transfer assembly.

Referring now to FIG. 7, an exploded view of the HTA modules 742 is shown. The gaseous medium passing through the flow tunnels 748 is cooled. A TEC array 750 in thermal contact with the flow tunnels 748 removes heat therefrom. A TEC array 750 may be disposed on either side of the flow tunnels 748. Heat sinks 752 are disposed on an outside of the TEC arrays 750 to remove heat therefrom. The flow tunnels 748 have inlets and outlets. To cool the gaseous medium flowing therethrough, various embodiments utilize flow tunnels 748 thermally coupled to one or more banks of TEC arrays 750. In the embodiment shown, the flow tunnels 748 are sandwiched between a plurality of TEC arrays 750. As will be explained in more detail below, in some embodiments, the flow tunnels 748 are formed having low-profile extrusions, or microtubes, running therethrough. In some embodiments, the microtubes have a plurality of microchannels running along an inside surface thereof.

Figure 8:
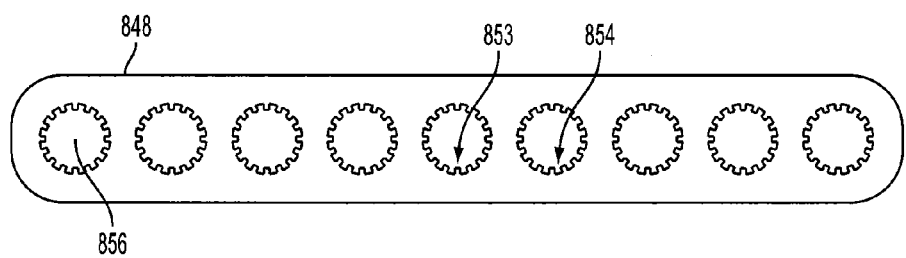
FIG. 8 is a cross-sectional view of an flow tunnel having a plurality of microtubes.

Referring now to FIG. 8, a cross-sectional view of an flow tunnel 848 can be seen. The flow tunnel 848 is formed from a heat conductive material adapted to transfer heat between a plurality of TEC arrays (not shown) and a gaseous medium flowing through the flow tunnels 848. The flow tunnels 848 also have a plurality of microtubes 856 therein to facilitate airflow therethrough. As can be seen from the embodiment shown, the microtubes 856 are adapted to have microchannels 854 running along an interior surface thereof thereby increasing the surface area of the interior of the microtubes 856. The microchannels 854 may be formed from surface enhancers 853 extending from the interior surface of the microtubes 856. The surface enhancers 853 provide an increased area of contact between the gaseous medium flowing thereby thus increasing the thermal conduction therebetween. One way of calculating the hydraulic diameter, or the flow area, of a microtube 856 is to measure the diameter of the area of the microtube 856 including the depth of the microchannels 854 and subtract the area of the surface enhancers 853. Another way of calculating the hydraulic diameter of a microtube 856 is to measure the area of the microtube excluding the depth of the microchannels 854 and add the of the microchannels 854. The two above mentioned calculations should result in a same hydraulic diameter, that is the cross-sectional area available for the gaseous medium to flow therethrough.

The surface enhancers 853 may also increase the Reynolds number of the flow path. In fluid mechanics, an increased Reynolds number is indicative of relatively turbulent flow while a decreased Reynolds number is indicative of a relatively laminar flow. At high Reynolds numbers, the turbulent flow may include competing inertial forces, which may produce random eddies, vortices, and other flow fluctuations. In some embodiments, it may be desirable to have the surface enhancers 853 adapted to increase the Reynolds number and thus create a turbulent flow profile within the microtubes 856. The increased turbulence may increase the amount of heat exchanged between the flow tunnels 848 and the gaseous medium flowing therethrough.

In some embodiments, an upper edge the microtubes 856, for example, an in the microtube 856, may be chamfered, or beveled or otherwise machined, to create a conically shaped opening at the inlet thereof. In some embodiments, a plurality of microchannels 854 may be disposed around an interior surface of the microtubes 856 to form a, for example, starburst-like shape. Various embodiments utilizing microchannels 854 and surface enhancers 853, may increase the contact area between the flow tunnels 848 and the gaseous medium flowing therein by as much as 30 to 40%. In some embodiments, the flow tunnels 848 are made of a thermally conductive material, such as, for example, aluminum, but the flow tunnels 848 can be made of any material that will allow thermal conductivity between the flow tunnels 848 and the gaseous medium flowing therethrough.

Figure 9:
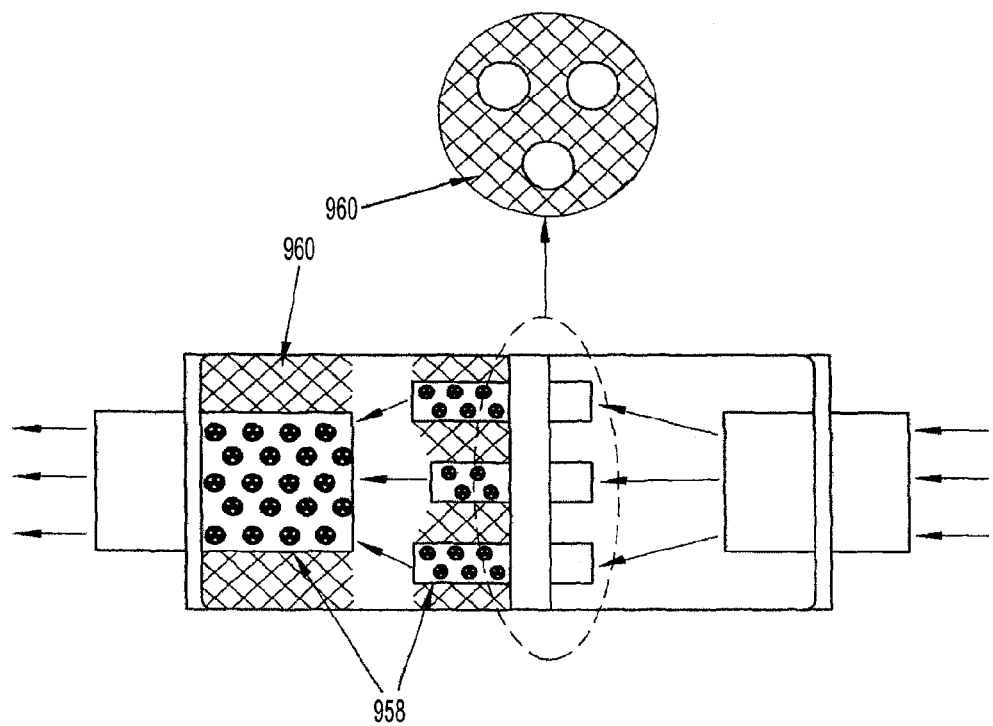
FIG. 9 is a cross-sectional view of an intake silencer.

Referring now to FIG. 9, a cross-section of an embodiment of an intake silencer 922 is shown. The ability to reduce noise caused by airflow may be desirable in many applications, for example, where the environment the control unit is being operated in is relatively quite. In some embodiments, acoustic baffles may be used to minimize audible noises caused by the control unit, for example, in the 15 dB range caused by, for example, the howling or whistling effects of an air mover. The intake silencer 922 may have a single intake port that then has the airflow separated into a plurality of flow paths through a plurality of tubes. The plurality of tubes may then have a plurality of perforations allowing the gaseous medium to exit through the plurality of perforations. Additionally, a filler, such as polyester, may be disposed between the plurality of tubes and the exit port. The exit port may also have a plurality of perforations therein to allow the air to pass therethrough.

Figure 10:
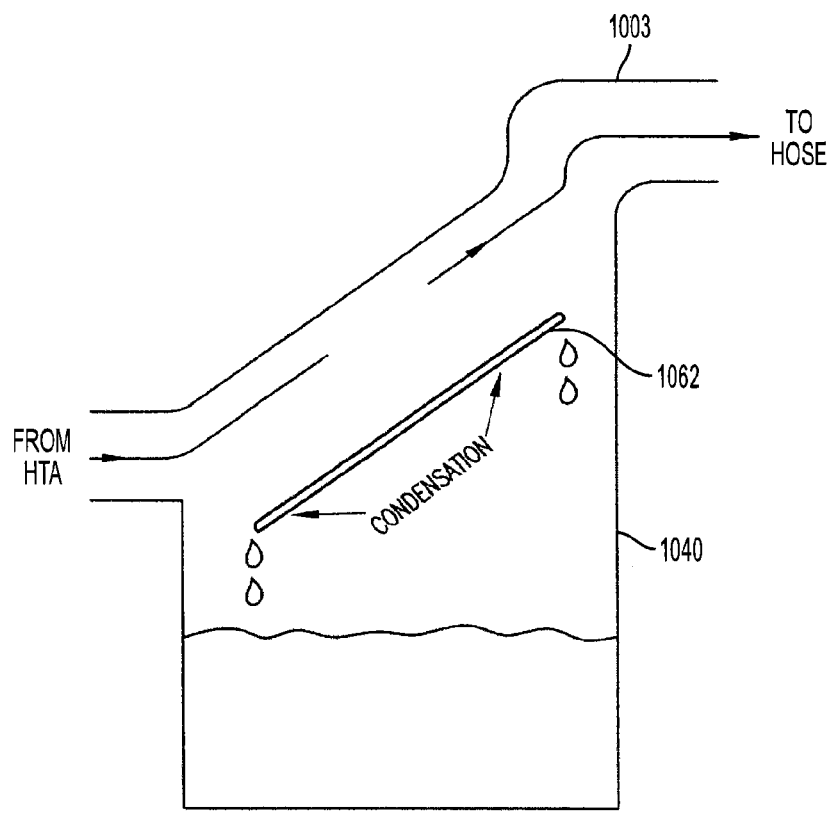
FIG. 10 is a diagram of a condensate trap.

Referring now to FIG. 10, a side view of a cross-section of a bottom chamber 1040 can be seen. After the gaseous medium has been cooled by the HTA modules (not shown), the gaseous medium flows to the bottom chamber 1040, as shown. The gaseous medium flows through the bottom chamber 1040 and out the hose interface 1003 to the delivery hose 1004 for use in a dermal application. To minimize the water content of the cooled gaseous medium delivered to the patient, a condensate trap 1062 is provided in the bottom chamber 1040. For example, in some embodiments, the condensate trap 1062 is placed at a 45° angle relative to the flow path. As the gaseous medium flows across the surface of the condensate trap 1062, moisture in the gaseous medium condenses on the surface of the condensate trap 1062. Similarly, any water particles or other moisture will hit the condensate trap 1062 and flow down therefrom.

In some embodiments, the amount of condensation collecting in the drip pan of the bottom chamber 1040 may be monitored. In some embodiments, a level monitor monitors the amount of condensation, for example the water level inside the drip pan. In some embodiments, the conditions at which the control unit is being run are monitored and the amount of condensation is predicted. For example, the humidity of the gaseous medium being cooled and the amount of cooling being done may be used as an indicator of the amount of condensation that will accumulate. In some embodiments, an alarm may alert a user that the drip pan needs to be emptied. In some embodiments, a drain may be attached to the drip pan to allow drainage of the condensate. In some embodiments, a valve, such as a solenoid valve, may be utilized to allow the drip pan to be drained automatically.

The previous description is of a preferred embodiment for implementing the invention, and the scope of the invention should not necessarily be limited by this description. The scope of the present invention is instead defined by the following claims.

What is claimed is:

1. A method of thermally affecting a gaseous medium for dermatological applications, the method comprising:
- providing a plurality of thermally controlled flow tunnels;
- creating a pressure differential to impart airflow through the plurality of flow tunnels for thermal interaction therewith;
- actively cooling the plurality of flow tunnels to a temperature below a freezing point of moisture contained within the gaseous medium;
- monitoring a condition relating to the airflow of the gaseous medium flowing through the flow tunnels; and
- reducing the level of active cooling of at least one of the plurality of flow tunnels in response to a monitored condition indicative of a reduction in a hydraulic diameter of at least one of the plurality of flow tunnels.

2. The method of claim 1 wherein the condition is a pressure of the gaseous medium.

3. The method of claim 1 wherein the condition is a flow rate of the gaseous medium.

4. The method of claim 1 and further comprising:
- actively heating at least one of the plurality of flow tunnels.

5. The method of claim 1 and further comprising:
- monitoring a temperature of the gaseous medium exiting the flow tunnels;
- providing the gaseous medium to a remotely disposed location via a delivery hose, the delivery hose having a thermal conductivity and a length; and
- determining a temperature of the gaseous medium at the remotely disposed location based on the thermal conductivity and the length.

6. The method of claim 1 and further including drawing the gaseous medium from ambient air.

7. The method of claim 6 wherein the air contains moisture in the form of water and the reduction in hydraulic diameter is the result of the moisture solidifying into an ice formation in the flow tunnel.

8. The method of claim 7 wherein the reducing the level of active cooling includes melting the ice formation.

* * * * *

UNITED STATES PATENT AND TRADEMARK OFFICE
CERTIFICATE OF CORRECTION

PATENT NO. : 8,414,631 B2  Page 1 of 1
APPLICATION NO. : 12/524592
DATED : April 9, 2013
INVENTOR(S) : Tony Quisenberry et al.

It is certified that error appears in the above-identified patent and that said Letters Patent is hereby corrected as shown below:

In the Specification
Column 11, Line 21

Replace "edge the microtubes 856,"
With -- edge of the microtubes 856, --

Column 11, Line 22

Replace "an in the microtube 856,"
With -- an inlet of the microtube 856, --

Signed and Sealed this
Twenty-fifth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,414,631 B2  
APPLICATION NO. : 12/524592  
DATED : April 9, 2013  
INVENTOR(S) : Quisenberry et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 847 days.

Signed and Sealed this
First Day of September, 2015

Michelle K. Lee
*Director of the United States Patent and Trademark Office*